(12) United States Patent
Wei et al.

(10) Patent No.: US 7,514,106 B2
(45) Date of Patent: Apr. 7, 2009

(54) COMPOSITIONS AND METHODS FOR UTERINE RELAXING

(75) Inventors: Chia-Li Wei, Keelung (TW);
Meng-Hwan Lee, Yunlin County (TW);
Chun-Ying Lin, Taipei County (TW);
Jay Hua, Hsinchu (TW); Ying-Chieh Tsai, Taipei (TW)

(73) Assignee: Yangsen Biotechnology Co., Ltd., Taipei (TW)

( * ) Notice: Subject to any disclaimer, the term of this patent is extended or adjusted under 35 U.S.C. 154(b) by 0 days.

(21) Appl. No.: 11/892,630

(22) Filed: Aug. 24, 2007

(65) Prior Publication Data
US 2008/0113049 A1  May 15, 2008

Related U.S. Application Data

(63) Continuation-in-part of application No. 11/392,698, filed on Mar. 30, 2006, now abandoned.

(51) Int. Cl.
*A01N 65/00* (2006.01)

(52) U.S. Cl. ........................ 424/725; 514/899

(58) Field of Classification Search ........................ None
See application file for complete search history.

(56) References Cited

FOREIGN PATENT DOCUMENTS

| | | | |
|---|---|---|---|
| CN | 1552382 | * | 12/2004 |
| CN | 1624095 A | * | 6/2005 |
| JP | 2003212779 A | * | 7/2003 |

OTHER PUBLICATIONS

Risch, Spices: Flavor, sources, processing and chemistry, Book of Abstracts, 211 th ACS national Meeting, New Orleans, LA, Mar. 24-28, 1996, AGFD-053. American Chemical Society: Washington, D.C.*
Yonzon et al., Antimicrobial activities of essential oils of Napel, Journal of essential oil research, 17 (1): 107-111, 2005.*
P. Murata et al., Phytother. Res. 15, pp. 302-306(2001).
S. Burt, International Journal of Food Microbiology 94 (2004) pp. 223-253.
S.N. Ostad et al., Journal of Ethnopharmacology 76 (2001) pp. 299-304.
Chinese Traditional Patent Medicine vol. 22 No. 10, Oct. 2000, pp. 717-719.
Yonzon et al., Antimicrobial activities of essential oils of Nepal. J. Essent. Oil Res., 17: 107-111, 2005.
S. N. Ostad et al, "The Effect of Fennel Essential Oil on Uterine Contraction as a Model for Dysmenorrhea, Pharmacology and Toxicology Study", Journal of Ethnopharmacology 76, (Apr. 11, 2001) pp. 299-304.

(Continued)

Primary Examiner—Michele Flood
Assistant Examiner—Qiuwen Mi
(74) Attorney, Agent, or Firm—Muncy, Geissler, Olds & Lowe, PLLC

(57) ABSTRACT

A method for treating/relief of women's menstruation pain. The pain is reduced or relieved by externally administering an effective amount of an essential oil obtained from anthopogon.

15 Claims, 1 Drawing Sheet

OTHER PUBLICATIONS

Mitsutoshi Satoh et al, "Effects of Acute and Short-Term Repeated Application of Fullerene $C_{60}$ on Agonist-Induced Responses in Various Tissues of Guinea Pig and Rat", Gen. Pharmac. vol. 26, No. 7 (Dec. 22, 1994) pp. 1533-1538.

Yuming Dong et al, "Study on the Chemical Compounds In the Volatile Oils from Leaves of Rhododendron Anthopogonodies", Departmetn of Pharmaceutical Analysis, School of Pharmacy, Lanzhou Medical College, Lanzhou, J. Lanzhou Med. Coll. (Sep. 2003), vol. 29, pp. 15, 16 and 32.

* cited by examiner

COMPOSITIONS AND METHODS FOR UTERINE RELAXING

CROSS REFERENCE TO RELATED APPLICATIONS

The application is a Continuation-In-Part of U.S. patent application Ser. No. 11/392,698, filed on Mar. 30, 2006 now abandoned.

BACKGROUND OF THE INVENTION

1. Field of the Invention

The present invention relates to pharmaceutical compositions, and in particular relates to pharmaceutical compositions and methods for relieving menstruation pain.

2. Description of the Related Art

It is common for women to experience painful cramps when they have their monthly period (menstruation), especially at their young age. Some women also get some pain or a feeling of congestion in the abdomen in the days before their period. Every month while women are in their reproductive years, the uterus builds up the endometrium (inner lining of the uterus) with blood and other fluids. The endometrium is intended to provide the nourishment that an embryo would need if the woman were to become pregnant. If, after ovulation (release of an egg into the uterus or womb), the woman does not become pregnant, then the uterus sheds the endometrium over a few days (menstruation or period).

Therefore, the muscles in the uterus contract and then relax, to squeeze the endometrium, break it down and get it moving out of the uterus. The fluid leaves the uterus through the cervix, and then flows out of the woman's body through the vagina. Most contractions of the muscles in the uterus are not felt. Sometimes, though, contractions are strong and frequent, causing pain. These are often called menstrual cramps. Period pain can be felt just in the abdomen, or it can spread up and around the back, and down die legs. Some women also experience nausea, vomiting or even diarrhea.

The medical term for painful periods is dysmenorrhea. Most women (as many as 70% of women) will get some amount of pain when they have a period. For about one in ten of these women, that pain can be so bad that for one to three days each month they are unable to carry on with their lives normally. Period pain, as well as severe period pain, is even more common in teenage women, affecting as many as 70% to 90% of teenagers. After a teenage woman has been menstruating for a few years, the pain is likely to at least reduce, and will stop for some. Many women will also have less period pain after they have a baby.

Medically, there are two categories, of period pain: primary and secondary. Primary period pain is when it is only the menstrual cramps causing the pain. Secondary period pain is caused by a disease or condition (such as cysts on the ovaries, or endometriosis—where endometrium grows in other places than the uterus). If period pain is severe or getting worse, it needs to be investigated by a doctor to evaluate the possible cause.

In addition to taking over-the-counter analgesic, one treatment for period pain is to regulate or reduce levels of prostaglandin (PQ) by taking either the oral contraceptive pill (the pill), or NSAIDs (non-steroidal anti-inflammatory drugs). PGs will cause the uterine muscles to contract to get the endometrium moving out of the uterus and the contractions (cramps) may cause pain.

In spite of their effectiveness, the presence of side effects from these drugs to liver, kidneys and digestive system limit their clinical use. A feasible alternative of natural herb therapy needs therefore to be considered.

BRIEF SUMMARY OF THE INVENTION

An object of the invention is to provide period pain-relieving essential oils for women when it is applied in an amount by which sufficient uterine relaxing effect can be obtained.

In an embodiment, a method for treating/relief of women's menstruation pain is provided by administrating a uterine relaxing composition with a sufficient amount of an essential oil extracted from *Rhododendron anthopogon* (anthapogon), which can be used to reduce or relieve women's menstruation pain and dysmenorrhea. In another embodiment, the essential oil of *Rhododendron anthopogon* can be administrated directly without mixed with any compounds or excipient, A detailed description is given in the following embodiments and experiment results.

BRIEF DESCRIPTION OF THE DRAWINGS

The present invention can be move fully understood by reading the subsequent detailed description and examples with references made to the accompanying drawings, wherein.

DETAILED DESCRIPTION OF THE INVENTION

Figure 1:
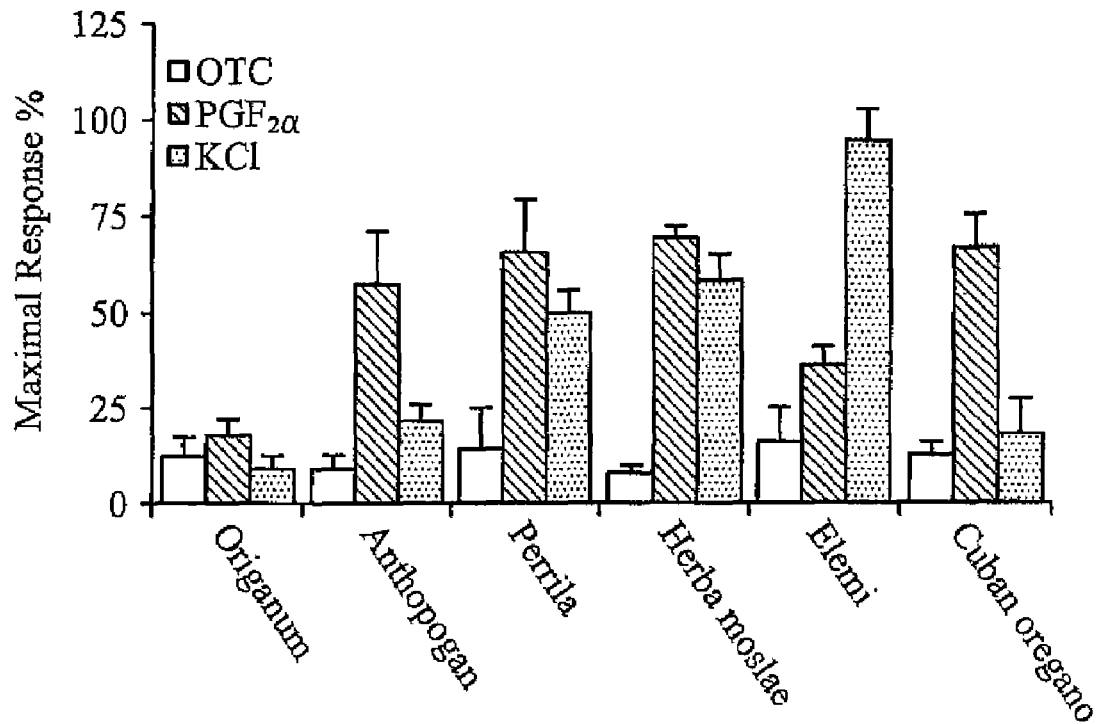
FIG. 1 shows the inhibitory effects of essential oils from origanum, anthopogon, perrila, herba moslae, elemi and cuban oregano on oxytocin- (OTC-), $PGF_{2a}$- and KCl-stimulated rat uterine muscle contraction.

The following description is of the best-contemplated mode of carrying out the invention. This description is made for the purpose of illustrating the general principles of the invention and should not be taken in a limiting sense. The scope of the invention is best determined by reference to the appended claims.

Essential oils, also called volatile or ethereal oils, are aromatic oily liquids obtained by expression, fermentation, enfleurage or extraction from plant material such as flowers, buds, seeds, leaves, twigs, baric, herbs, wood, fruits and roots, referring to "Essential oils: their antibacterial properties and potential applications in foods—a review" (Sara Burt, International Journal of Food Microbiology 2004; 94: 223-53). Essential oils are usually composed of tiny molecules, this allows them to penetrate the skin easily and work into the body during externally topical use.

The essential oil of anthopogon can be extracted from anthopogon growing wildly in the west Nepal. In an embodiment, the essential oil of anthopogon is extracted with the shoot portions, e.g. the stems, leaves, flowers, by water/steam distillation. However, the essential oil of anthopogon can be obtained by other common extraction procedures, such as expression, fermentation, or enfleurage, in other embodiments.

In an embodiment, a method for treating/relief of women's menstruation pain by administrating a uterine relaxing composition with a sufficient amount of an essential oil extracted from *Rhododendron anthopogon* (anthopogon), which can be used to reduce or relieve women's menstruation pain and dysmenorrhea. The composition can be in any form, e.g. gel, cream, medical plaster, liquid, powder, or capsule. The composition can also be a mixture of essential oils, including a sufficient amount of anthopogon essential oil with other essential oils, base oils/carry oils, base creams/carry creams, or base gels/carry gels. The composition can be administrated externally on the female's skin or abdomen, or orally, depending on the form of the composition. In another embodiment, the essential oil of *Rhododendron anthopogon* can be administrated directly without mixed with any compounds or excipient.

According to the invention, it is found that six essential oils obtained from origanum, anthopogon, perrila, herba moslae, elemi, and cuban oregano are effective for uterine relaxing, which will be helpful for period pain relieving by external use.

EXPERIMENT RESULTS OF UTERINE RELAXING ACTIVITY

TABLE 1

Materials-Essential oil

| Essential oil sample | Common name | Scientific name |
|---|---|---|
| A | origanum | *Origanum vulgare* |
| B | anthopogon | *Rhododendron anthopogon* |
| C | perrila | *Perilla frutescens* |
| D | herba moslae | *Mosla chinensis* |
| E | elemi | *Canarium luzonicum* |
| F | cuban oregano | *Plectranthus amboinicus* |

The essential oils of origanum, anthopogon, perrila, herba moslae and elemi were purchased from HengYi Trading Co., Ltd. (Taiwan), Natural Resources Industries (P) Ltd. (Nepal), Jiangxi Jishui TongRen Natural & pharmaceutical oil factory (China), HuaLong Magnolia Development Co., Ltd. (China) and A. M. Aromatic & Essential Oils (India), respectively. Essential oil of cuban oregano was extracted by hydrodistillation of leaf of the plant from Taiwan using a Clevenger-type apparatus.

The essential oil of anthopogon used in the above experiment was obtained by steam distillation of the shoot portions, i.e. the stems, leaves and flowers of anthopogon growing wildly in the west Nepal. However, the essential oil of anthopogon can also be obtained by other extraction process from the whole plant. Further, cultivated anthopogon in Nepal or other places can also be used to obtain the anthopogon essential oil.

Uterine Relaxing Activity

Uterine relaxing activities on OTC- and KCl-stimulated rat uterine muscle contraction were carried out according to the method described by Ostad S N, Soodi M, Shariffzadeh M, Khorshidi N, and Marzban H. (The effect of fennel essential oil on uterine contraction as a model for dysmenorrhea, pharmacology and toxicology study. Journal of Ethnopharmacology 2001; 76: 299-304.). Female virgin Sprague-Dawley rats (200 g to 300 g) were obtained from the Laboratory Animal Center at Yang-Ming University. They were primed with 5 mg/kg of estradiol (Sigma-Aldrich) 24 hours before the experiments, and then sacrificed by $CO_2$ asphyxiation. Uterine strips free from adhering tissues were mounted under a resting tension of 1 g in a 10 ml organ bath containing dejalon solution gassed with carbogen (95% $O_2$ and 5% $CO_2$) at 31° C., which were then allowed to equilibrate for at least 1 hour. To evaluate the effect on the contractile response induced by $PGF_{2a}$, a modified Locke-Ringer solution and a maintained temperature of 28° C. were used according to the method described by Murata. P, Hayakawa T, Satoh K, Kase Y, Ishige A, and Sasaki H. (Effects of Dai-kenchu-to, a herbal medicine, on uterine and intestinal motility. Phytotherapy Research 2001; 15: 302-6). Contractions were recorded by force displacements transducers (Grass Instruments USA) using MP100 workstation software (Biopac Systems USA) on a PC. The results of inhibitory activities of the essential oils are shown in FIG. 1.

FIG. 1 shows the comparison of the inhibitory effects of essential oils from origanum, anthopogon, perrila, herba moslae, elemi and cuban oregano on OTC-, $PGF_{2a}$- and KCl-stimulated rat uterine muscle contraction. The muscle strip was pretreated with 80 µg/ml of essential oils for 10 min before OTC (10 mU/ml), $PGF_{2a}$ (1 µM) or KCl (60 mM) treatment. The maximal response percentage represents the muscle contraction degree after treatment, comparing with no essential oil pretreatment as the control group (100%). Data were presented as mean ±standard error of three independent experiments. As shown in FIG. 1, for OTC-stimulated rat uterine muscle contraction, the muscle contraction responses for all six essential oils are 8% to 16%, which indicates that these essential oils is effective for inhibiting 84% to 92% uterine muscle contraction than the control group (i.e. no essential oil treatment). Similarly, for $PGF_{2a}$-stimulated rat uterine muscle contraction, origanum and elemi show the strongest inhibition (82% and 66%, respectively ) of muscle contraction, and anthopogon, perrila, herba moslae, and cuban oregano show moderate inhibition (31% to 43%) as well. For KCl-stimulated rat uterine muscle contraction, origanum, anthopogon, and cuban oregano show 78% to 91% inhibition. Perrila and herba moslae also show moderate inhibition (50% and 42%, respectively) of muscle contraction.

Dysmenorrhea Model in Mice

Another dysmenorrhea model in mice by Yang et al. (Yang M.-H., Jin Z.-H., Guo Y.-F., Zhu P.-Q., Chen W.-J. Study on regulation action of Tiaojinghuoxue capsules on menstruation. Chinese Traditional Patent Medicine 2000; 22; 717-9.) with modifications was also conducted to evaluate the activity of the essential oils. Thirty-six female ICR mice (30 g to 40 g) from the Laboratory Animal Center at National Taiwan University College of Medicine were grouped into three. One ml/kg of jojoba oil, origanum or anthopogon essential oils (30% in jojoba oil, respectively) were rubbed on belly of mice once a day during days 1-5 and 8-12, followed by intraperitoneal injection of diethylstilbestrol (10 mg/kg) once a day during days 9-11. After 30 min of oil rubbing on day 12, OTC (15 U/kg) was intraperitoneally injected and the induced twisting numbers in 30 min were recorded. The experiment results are shown in TABLE 2.

TABLE 2

Effects of essential oils from origanum and anthopogon on dysmenorrhea mouse

| Groups | Number of twisting mouse | Twisting number[a] | Twisting percent |
|---|---|---|---|
| jojoba | 12 | 21.8 ± 8.1 | 100 |
| origanum | 12 | 5.1 ± 5.3 | 23 |
| anthopogon | 12 | 5.9 ± 4.4 | 27 |

[a]Mean ± standard error was shown.

A similar dysmenorrhea model experiment was also conducted for herba moslae and perrila essential oils and the experiment results are shown in TABLE 3.

TABLE 3

Effects of essential oils from herba moslae and perrila on dysmenorrhea mouse

| Groups | Number of twisting mouse | Twisting number[a] | Twisting percent |
|---|---|---|---|
| jojoba | 12 | 14.5 ± 6.2 | 100 |
| herba moslae | 12 | 6.9 ± 4.2 | 48 |
| perrila | 12 | 3.8 ± 3.5 | 26 |

[a]Mean ± standard error was shown.

According to the results shown in TABLE 2 both origanum and anthopogon essential oils could decrease the twisting times (77% and 73%) of dysmenorrhea mice induced by OTC, comparing to the control group (jojoba oil). According to the results shown in TABLE 3, both perrila and herba moslae oils could also decrease the twisting times (74% and 52%) of dysmenorrhea mice.

Chemical Analysis of the Essential Oils

The content of the six essential oils were further analyzed by gas chromatography-mass spectrometry (GC-MS). The chemical composition of each essential oil was determined using an Agilent 6890N gas chromatography, equipped with a HP-5MS capillary column (30 m×0.25 mm; film thickness; 0.25 μm) and an Agilent 5973 mass spectrometer as detector. Injector and detector (MS transfer line) temperatures were set at 250° C. and 285° C., respectively. The carrier gas was helium (1 ml/min), and 1 μl of diluted sample (1/10 in isopropanol) was injected by an autosampler (Agilent 7683 Series). The oven temperature was programmed as follows: 40° C. (5 min), 40° C. to 180° C. (3° C. $\min^{-1}$), 180° C. to 200° C. (6° C. $\min^{-1}$), 200° C. to 250° C. (8° C. $\min^{-1}$), and 250° C. (3 min.). The oil components were identified by comparison of their retention indices and mass spectra with the GC-MS computer database (Wiley 275.L). Parts of the content results of the six essential oils are shown in TABLE 4.

TABLE 4

Content percentage of compounds identified by GC-MS from the essential oils

| Compound | Content % of compounds identified by GC-MS from the essential oils | | | | | |
|---|---|---|---|---|---|---|
| | origanum | anthopogon | perrila | herba moslae | elemi | cuban oregano |
| carvacrol | 35.66 | — | — | 6.39 | — | 57.98 |
| 1-β-pinene | — | 6.92 | — | — | — | — |
| limonene | — | 8.77 | 20.32 | 31.36 | 29.28 | 1.24 |
| thymol | 30 | — | — | 3.54 | — | — |
| linalool | 6.05 | — | 1.38 | — | — | 0.20 |

A comparison of the inhibitory effects of carvacrol, 1-β-pinene, limonene, thymol and linalool on OTC-, $PGF_{2\alpha}$- and KCl-stimulated rat uterine muscle contraction was conducted. The muscle strip was pretreated with 20 μg/ml of compounds for 10 min before OTC (10 mU/ml), $PGF_{2\alpha}$ (1 μM) or KCl (60 mM) treatment. The maximal response percentage represents the muscle contraction degree after treatment, comparing with no essential oil pretreatment as the control group (100%). Data were presented as mean ±standard error of three independent experiments. The results are shown in FIG. 2.

Figure 2:
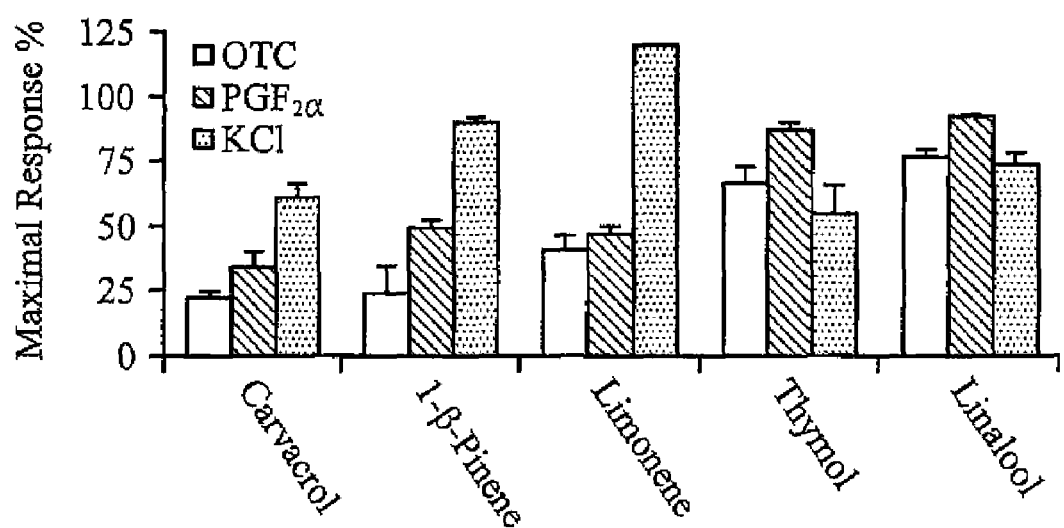
FIG. 2 shows the inhibitory effects of carvacrol, 1-β-pinene, limonene, thymol and linalool on OTC-, $PGF_{2a}$- and KCl-stimulated rat uterine muscle contraction.

As shown in FIG. 2, for OTC-stimulated rat uterine muscle contraction, carvacrol, 1-β-pinene, limonene, thymol and linalool all relieve the muscle contraction responses (24% to 78%). For $PGF_{2\alpha}$-stimulated rat uterine muscle contraction, carvacrol, 1-β-pinene and limonene show 51% to 66% inhibition of muscle contraction, whereas thymol and linalool didn't show obvious inhibition; For KCl-stimulated rat uterine muscle contraction, carvacrol, thymol and linalool show 27% to 46% of inhibition.

According to the above experiment results, it is shown that all six essential oils from origanum, anthopogon, perrila, herba moslae, elemi, and cuban oregano exhibit relaxing activity of uterine muscle contraction in different degrees and thereby the six essential oils can be used solely or in combination as a uterine relaxing composition for treating period pain or dysmenorrhea. Moreover, the compounds, carvacrol, 1-β-pinene, limonene, thymol and linalool, isolated from the six essential oils, also show relaxing activity of uterine muscle contraction, and thereby, the compounds can also be used as a uterine relaxing composition for treating period pain or dysmenorrhea.

While the invention has been described, by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for treating or relieving menstruation pain by administering a uterine relaxing composition to a subject in need thereof comprising a sufficient amount of an essential oil extracted from *Rhododendron anthopogon*.

2. The method as claimed in claim 1, wherein the essential oil extracted from *Rhododendron anthopogon* is obtained by water distillation of *Rhododendron anthopogon*.

3. The method as claimed in claim 1, wherein the essential oil extracted from *Rhododendron anthopogon* is obtained from shoot portions thereof.

4. The method as claimed in claim 3, wherein the essential oil extracted from *Rhododendron anthopogon* is obtained by steam distillation of *Rhododendron anthopogon*.

5. The method as claimed in claim 1, wherein the essential oil extracted from *Rhododendron anthopogon* is obtained by expression, fermentation or enfleurage of *Rhododendron anthopogon*.

6. The method as claimed in claim 1, wherein the uterine relaxing composition is administered externally.

7. The method as claimed in claim 1, wherein the *Rhododendron anthopogon* is obtained from Nepal.

8. The method as claimed in claim 1, wherein the uterine relaxing composition further comprises another essential oil, base oil base cream, or base gel.

9. The method as claimed in claim 1, wherein the uterine relaxing composition is in the form of a gel, cream, medical plaster, liquid, powder, or capsule.

10. A method for treating or relieving menstruation pain by administering a sufficient amount of an essential oil extracted from *Rhododendron anthopogon*.

11. The method as claimed in claim 10, wherein the essential oil extracted from *Rhododendron anthopogon* is obtained from shoot portions thereof.

12. The method as claimed in claim 10, wherein the essential oil extracted from *Rhododendron anthopogon* is obtained by steam distillation of *Rhododendron anthopogon*.

13. The method as claimed in claim 10, wherein the essential oil extracted from *Rhododendron anthopogon* is administered externally.

14. The method as claimed in claim 10, wherein the essential oil extracted from *Rhododendron anthopogon* is obtained by expression, fermentation or enfleurage of *Rhododendron anthopogon*.

15. The method as claimed in claim 10, wherein the *Rhododendron anthopogon* is obtained from Nepal.

* * * * *